(12) United States Patent
Greenhut et al.

(10) Patent No.: US 10,765,870 B2
(45) Date of Patent: *Sep. 8, 2020

(54) METHOD AND APPARATUS FOR DETECTION OF INTRINSIC DEPOLARIZATION FOLLOWING HIGH ENERGY CARDIAC ELECTRICAL STIMULATION

(71) Applicant: Medtronic, Inc., Minneapolis, MN (US)

(72) Inventors: Saul E. Greenhut, Denver, CO (US); Michael T. Hemming, Kiowa, CO (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/196,320

(22) Filed: Nov. 20, 2018

(65) Prior Publication Data

US 2019/0083790 A1    Mar. 21, 2019

Related U.S. Application Data

(63) Continuation of application No. 15/450,182, filed on Mar. 6, 2017, now Pat. No. 10,130,818, which is a (Continued)

(51) Int. Cl.
*A61N 1/00*  (2006.01)
*A61N 1/37*  (2006.01)
(Continued)

(52) U.S. Cl.
CPC .......... *A61N 1/3702* (2013.01); *A61B 5/0422* (2013.01); *A61B 5/0452* (2013.01);
(Continued)

(58) Field of Classification Search
CPC .. A61N 1/3702; A61N 1/3621; A61N 1/3625; A61N 1/3622; A61N 1/3925;
(Continued)

(56) References Cited

U.S. PATENT DOCUMENTS

| 4,537,201 A | 8/1985 | Delle-Vedove et al. |
| 5,354,316 A | 10/1994 | Keimel |

(Continued)

FOREIGN PATENT DOCUMENTS

WO    9448893 A1    11/1998

OTHER PUBLICATIONS (PCT/US2016/028246) PCT Notification of Transmittal of the International Search Report and the Written Opinion of the International Searching Authority, dated Jul. 5, 2016, 10 pages.

*Primary Examiner* — Scott M. Getzow

(57) ABSTRACT

A medical device is configured to deliver a high-energy electrical stimulation pulse to a patient that produces a post-stimulation polarization signal. A cardiac signal analyzer of the medical device is configured to detect a cardiac electrical signal superimposed on the post-stimulation polarization signal, determine at least one feature of the detected cardiac electrical signal, compare the feature to criteria that differentiate an intrinsic cardiac event during the post-stimulation polarization signal from an evoked response signal and identify the detected cardiac electrical signal as the intrinsic cardiac event if the feature meets the criteria.

18 Claims, 5 Drawing Sheets

Related U.S. Application Data continuation of application No. 14/693,933, filed on Apr. 23, 2015, now Pat. No. 9,586,051.

(51) Int. Cl.

| | | |
|---|---|---|
| *A61N 1/39* | (2006.01) | |
| *A61B 5/0452* | (2006.01) | |
| *A61N 1/362* | (2006.01) | |
| *A61B 5/00* | (2006.01) | |
| *A61B 5/042* | (2006.01) | |
| *A61B 5/0464* | (2006.01) | |
| *G06K 9/00* | (2006.01) | |
| *A61B 5/021* | (2006.01) | |
| *A61B 5/0408* | (2006.01) | |
| *A61B 5/0456* | (2006.01) | |
| *A61B 5/11* | (2006.01) | |

(52) U.S. Cl.
CPC ............ *A61B 5/0464* (2013.01); *A61B 5/686* (2013.01); *A61N 1/3621* (2013.01); *A61N 1/3622* (2013.01); *A61N 1/3625* (2013.01); *A61N 1/371* (2013.01); *A61N 1/3925* (2013.01); *A61N 1/3956* (2013.01); *A61N 1/3962* (2013.01); *G06K 9/0053* (2013.01); *G06K 9/00543* (2013.01); *A61B 5/021* (2013.01); *A61B 5/0456* (2013.01); *A61B 5/04085* (2013.01); *A61B 5/1118* (2013.01)

(58) Field of Classification Search
CPC ............ G06K 9/0053; G06K 9/00543; A61B 5/0464; A61B 5/0422; A61B 5/686; A61B 5/0452; A61B 5/1118; A61B 5/0456; A61B 5/04085; A61B 5/021
See application file for complete search history.

(56) References Cited

U.S. PATENT DOCUMENTS

| | | |
|---|---|---|
| 5,417,718 A | 5/1995 | Kleks et al. |
| 5,443,485 A | 8/1995 | Housworth et al. |
| 5,545,186 A | 8/1996 | Olson et al. |
| 5,697,957 A | 12/1997 | Noren et al. |
| 5,843,137 A | 12/1998 | Condie et al. |
| 5,861,013 A | 1/1999 | Peck et al. |
| 5,871,512 A | 2/1999 | Hemming et al. |
| 5,873,898 A | 2/1999 | Hemming et al. |
| 6,134,473 A | 10/2000 | Hemming et al. |
| 6,144,881 A | 11/2000 | Hemming et al. |
| 6,163,724 A | 12/2000 | Hemming et al. |
| 6,393,316 B1 | 5/2002 | Gillberg et al. |
| 6,411,844 B1 | 6/2002 | Kroll et al. |
| 6,434,428 B1 | 8/2002 | Sloman et al. |
| 6,587,722 B2 | 7/2003 | Vitali et al. |
| 7,027,858 B2 | 4/2006 | Cao et al. |
| 7,031,771 B2 | 4/2006 | Brown et al. |
| 7,191,003 B2 | 3/2007 | Greenhut et al. |
| 7,236,825 B2 | 6/2007 | Wang |
| 7,593,771 B2 | 9/2009 | Yonce et al. |
| 8,160,684 B2 | 4/2012 | Ghanem et al. |
| 8,290,590 B2 | 10/2012 | Bohn et al. |
| 8,301,233 B2 | 10/2012 | Zhang et al. |
| 8,437,842 B2 | 5/2013 | Zhang et al. |
| 2003/0149452 A1 | 8/2003 | Tang et al. |
| 2003/0153957 A1 | 8/2003 | Bradley |
| 2005/0038478 A1 | 2/2005 | Klepfer et al. |
| 2005/0131478 A1 | 6/2005 | Kim et al. |

METHOD AND APPARATUS FOR DETECTION OF INTRINSIC DEPOLARIZATION FOLLOWING HIGH ENERGY CARDIAC ELECTRICAL STIMULATION

This application is a continuation of U.S. patent application Ser. No. 15/450,182, filed Mar. 6, 2017, entitled "METHOD AND APPARATUS FOR DETECTION OF INTRINSIC DEPOLARIZATION FOLLOWING HIGH ENERGY CARDIAC ELECTRICAL STIMULATION," which claims the benefit of U.S. patent application Ser. No. 14/693,933, now U.S. Pat. No. 9,586,051, filed Apr. 23, 2015, entitled "METHOD AND APPARATUS FOR DETECTION OF INTRINSIC DEPOLARIZATION FOLLOWING HIGH ENERGY CARDIAC ELECTRICAL STIMULATION," the content of both of which is incorporated by reference in their entirety.

TECHNICAL FIELD

The disclosure relates generally to implantable medical devices and, in particular, to a method and apparatus for sensing intrinsic cardiac electrical signals during post-stimulation polarization signals following high-energy cardiac electrical stimulation pulses.

BACKGROUND

A variety of implantable medical devices (IMDs) for delivering a therapy, monitoring a physiological condition of a patient or a combination thereof have been clinically implanted or proposed for clinical implantation in patients. Some IMDs may employ one or more elongated electrical leads carrying stimulation electrodes, sense electrodes, and/or other sensors. IMDs may deliver therapy to or monitor conditions of a variety of organs, nerves, muscle or tissue, such as the heart, brain, stomach, spinal cord, pelvic floor, or the like. Implantable medical leads may be configured to allow electrodes or other sensors to be positioned at desired locations for delivery of electrical stimulation or sensing of physiological conditions. For example, electrodes or sensors may be carried at a distal portion of a lead. A proximal portion of the lead may be coupled to an implantable medical device housing, which may contain circuitry such as signal generation circuitry and/or sensing circuitry.

Some IMDs, such as cardiac pacemakers or implantable cardioverter defibrillators (ICDs), provide therapeutic electrical stimulation to or monitor the heart of the patient via electrodes carried by one or more implantable leads. The leads may be transvenous, e.g., implanted in the heart through one or more veins, to position intracardiac electrodes. Other leads may be non-transvenous leads implanted outside the heart, e.g., implanted epicardially, pericardially, or subcutaneously. In either case, the electrical stimulation provided by the IMD may include signals such as pacing pulses, cardioversion shocks or defibrillation shocks to address abnormal cardiac rhythms such as bradycardia, tachycardia or fibrillation.

In some cases, the IMD senses signals representative of intrinsic depolarizations of the heart and analyzes the sensed signals to identify normal or abnormal cardiac rhythms. Upon detection of an abnormal rhythm, the device may deliver an appropriate electrical stimulation pulse or pulses to restore or maintain a more normal rhythm. For example, an IMD may deliver pacing pulses to the heart upon detecting asystole, tachycardia or bradycardia, and deliver cardioversion or defibrillation shocks to the heart upon detecting tachycardia or fibrillation.

SUMMARY

In general, the disclosure is directed to techniques for detecting intrinsic cardiac electrical signals after delivery of a high energy, therapeutic electrical stimulation pulse, such as a cardioversion/defibrillation (CV/DF) shock or a high energy transthoracic pacing pulse delivered to a patient's heart. An IMD operating in accordance with the techniques of this disclosure detects cardiac electrical signals during a post-stimulation polarization signal caused by the therapeutic electrical stimulation pulse. The detected cardiac electrical signal is identified as an intrinsic cardiac electrical signal based on criteria that discriminates the intrinsic cardiac signal from a cardiac evoked response signal.

In one example, the disclosure provides a method performed by a medical device comprising delivering a high-energy electrical stimulation pulse to a patient that produces a post-stimulation polarization signal, detecting a cardiac electrical signal superimposed on the post-stimulation polarization signal, determining at least one feature of the detected cardiac electrical signal, comparing the feature to criteria that differentiate an intrinsic cardiac event during the post-stimulation polarization signal from an evoked response signal, and identifying the detected cardiac electrical signal as the intrinsic cardiac event if the feature meets the criteria.

In another example, the disclosure provides a medical device comprising a therapy delivery module configured to deliver a high-energy electrical stimulation pulse to a patient that produces a post-stimulation polarization signal and a cardiac signal analyzer configured to receive an electrical signal developed across a pair of electrodes coupled to the medical device. The cardiac signal analyzer is configured to detect, from the received electrical signal, a cardiac electrical signal superimposed on the post-stimulation polarization signal, determine at least one feature of the detected cardiac electrical signal, compare the feature to criteria that differentiate an intrinsic cardiac event during the post-stimulation polarization signal from an evoked response signal, and identify the detected cardiac electrical signal as the intrinsic cardiac event if the feature meets the criteria.

In another example, the disclosure provides a non-transitory, computer-readable storage medium comprising instructions that, when executed by a processor of a medical device, cause the medical device to deliver a high-energy electrical stimulation pulse to a patient that produces a post-stimulation polarization signal, detect a cardiac electrical signal superimposed on the post-stimulation polarization signal, determine a feature of the detected cardiac electrical signal, compare the feature to criteria that differentiates an intrinsic cardiac event during the post-stimulation polarization signal from an evoked response signal, and identify the detected cardiac electrical signal as the intrinsic cardiac event if the feature meets the criteria.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1:
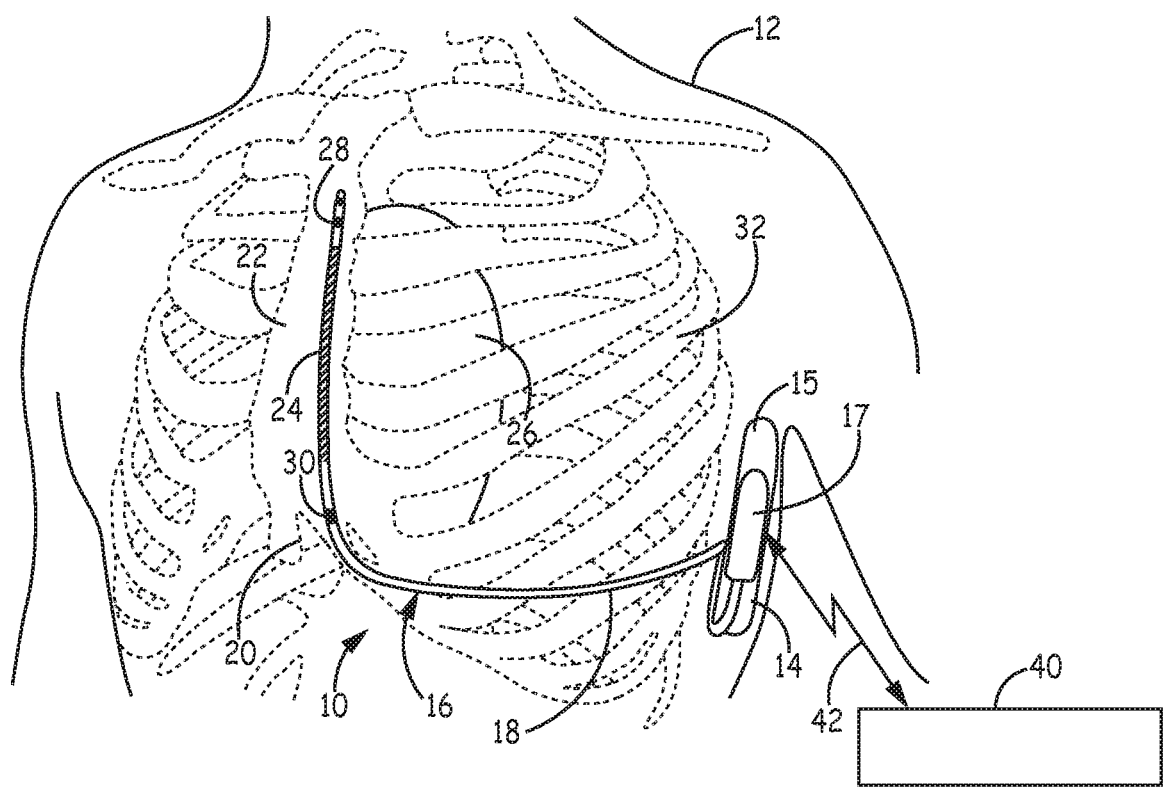
FIG. 1 is a conceptual diagram of a patient implanted with an example IMD system that includes an ICD coupled to a defibrillation lead.

In general, this disclosure describes techniques for sensing intrinsic cardiac electrical events that may occur during the polarization signal that is produced by therapeutic electrical stimulation pulses delivered to a patient. Immediately following delivery of an electrical stimulation pulse, such as a CV/DF shock pulse or an extracardiac pacing pulse, a residual post-stimulation polarization signal is generated by the charge induced in the patient's tissue by delivery of the stimulation pulse. If the stimulation pulse causes an evoked response in cardiac tissue, then an evoked response signal is superimposed on the large amplitude polarization signal.

Relatively high energy stimulation pulses are required to achieve therapeutic benefit when extracardiac electrodes, e.g., subcutaneous or substernal electrodes that are not in direct physical contact with the myocardium, are used to deliver the stimulation pulses compared to when stimulation pulses are delivered using electrodes that are in direct contact with the myocardium, e.g., intracardiac, endocardial, or epicardial electrodes. As used herein, a "high energy stimulation pulse" refers to an electrical stimulation pulse having a pulse energy that is on the order of milliJoules or higher. For example, extracardiac pacing pulses may be on the order of approximately 20 mJ to 140 mJ when biphasic, 200 mA extracardiac pacing pulses are delivered across an impedance load between 25 and 200 Ohms (resulting in a pulse amplitude range of 5 V to 40 V).

In contrast, pacing pulses delivered using endocardial or epicardial electrodes may be on the order of microJoules. Typical pacing pulses delivered using endocardial electrodes might be 2 V in amplitude with 0.5 ms pulse width across a load of between 400 and 1200 ohms, resulting in a typical pulse energy ranging from approximately 2 µJ to 60 µJ. Even at a maximum programmable voltage amplitude and pulse width, e.g., 8 V and pulse width of 1.5 ms (which would rarely be used), the pulse energy may be as high as approximately 240 µJ, but still well below the mJ range. As used herein, the term "approximately" when referring to a stated numerical value refers to a value within ±10% of the stated value The techniques disclosed herein for sensing intrinsic cardiac events during post-stimulation polarization signals may also be used following high energy electrical stimulation pulses delivered as CV/DF shocks. CV/DF shocks are even higher energy pulses than extracardiac pacing pulses, e.g., on the order of at least 10 Joules.

The relatively higher energy of extracardiac pacing pulses and of CV/DF shock pulses cause even higher amplitude polarization signals that decay over an even longer period of time than the polarization signals caused by lower energy pulses delivered via endocardial or epicardial electrodes. If an intrinsic cardiac event such as an R-wave occurs during the large polarization signal, the intrinsic cardiac event signal is superimposed on the polarization signal, and may occur during or after the evoked response signal. The large polarization signal interferes with sensing of intrinsic cardiac electrical events, such as R-waves, and therefore may interfere with the ability to sense the intrinsic heart rhythm by an ICD coupled to extracardiac electrodes. Without being able to reliably sense intrinsic cardiac events, the ICD or pacemaker may deliver unnecessary stimulation pulses, such as pacing pulses, in the presence of an adequate intrinsic heart rate.

When relatively lower energy pulses are delivered via endocardial or epicardial electrodes, the polarization signal is smaller and decays more quickly such that normal sensing of intrinsic cardiac signals is restored relatively soon after the stimulation pulse. A low polarization coating can be applied to the electrode surfaces to reduce the polarization signal making cardiac event sensing even more reliable in the presence of low energy stimulation pulses. Such coatings can be costly and may not be effective enough to reduce the larger polarization signals caused by higher energy stimulation pulses. The techniques described herein, however, may be used alone or in combination with low polarization coatings to enable an ICD to detect the intrinsic cardiac events superimposed on or occurring during the polarization signal.

Sensing of intrinsic cardiac events during delivery of high energy stimulation pulses is important because a pacing pulse delivered asynchronously with an underlying intrinsic rhythm could be delivered during the vulnerable period associated with myocardial repoloarization. Pacing during the vulnerable period can be pro-arrhythmic. Sensing of intrinsic R-waves that are attendant to the depolarization of the ventricular myocardium enables post-shock pacing or other electrical stimulation therapies to be properly timed or withheld in the presence of intrinsic cardiac events.

FIG. 1 is a conceptual diagram of a patient 12 implanted with an example IMD system 10 that includes an ICD 14 coupled to a defibrillation lead 16. Defibrillation lead 16 includes a proximal end that is connected to ICD 14 and a distal portion that includes one or more electrodes. Defibrillation lead 16 is illustrated in FIG. 1 as being implanted subcutaneously, e.g., in tissue and/or muscle between the skin and the ribcage 32 and/or sternum 22. In the example shown, defibrillation lead 16 extends subcutaneously from ICD 14 toward xiphoid process 20. At a location near xiphoid process 20, defibrillation lead 16 bends or turns and extends subcutaneously superior, substantially along sternum 22 or offset from sternum 22.

Figure 2:
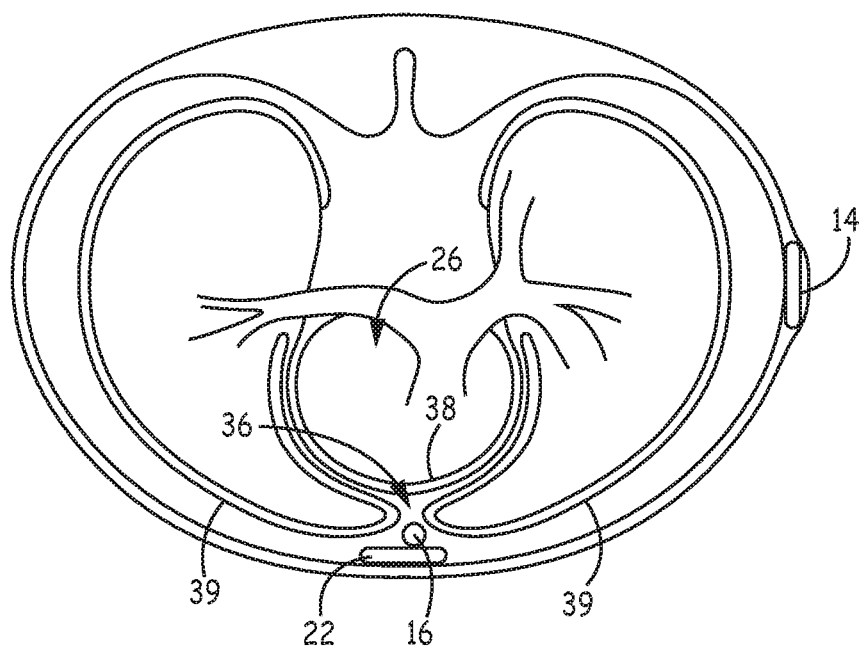
FIG. 2 is a transverse view of a patient implanted with an IMD system according to another example.

In other instances, lead 16 may be implanted at other extravascular or extracardiac locations. As shown in a transverse view of patient 12 in FIG. 2, lead 16 may be implanted at least partially in a substernal location, e.g., between the ribcage 32 and/or sternum 22 and heart 26. In one such configuration, a proximal portion of lead 16 extends subcutaneously from ICD 14 toward sternum 22 (not seen in the transverse view of FIG. 2) and the distal portion of lead 16 extends superior under or below the sternum 22 in the anterior mediastinum 36. Anterior mediastinum 36 is bounded laterally by pleurae 39, posteriorly by pericardium 38, and anteriorly by sternum 22. Lead 16 may be at least partially implanted in other intrathoracic locations, e.g., other non-vascular, extra-pericardial locations but not attached to the pericardium or other portion of heart 26.

Referring again to FIG. 1, lead 16 includes an elongated lead body 18 carrying electrodes 24, 28 and 30 located along the distal portion of the length of the lead body 18. Lead body 18 insulates one or more elongated electrical conductors (not illustrated) that each extend from a respective electrode 24, 28 and 30 through the lead body 18 to a proximal connector (not shown) that is coupled to ICD 14. Lead body 18 may be formed from a non-conductive material, such as silicone, polyurethane, fluoropolymers, or mixtures thereof or other appropriate materials, and may define one or more lumens within which the one or more conductors extend.

ICD 14 includes connector assembly 17 (sometimes referred to as a connector block or header) that includes a connector bore for receiving the proximal connector of lead 16 and electrical feedthroughs through which electrical connections are made between electrical conductors within lead 16 and electronic components included within the housing 15. The lead conductors are electrically coupled to ICD circuitry, such as a therapy delivery module and a sensing module, via connections in the ICD connector assembly 17 and associated electrical feedthroughs crossing ICD housing 15 as necessary. The electrical conductors transmit electrical stimulation pulses from a therapy delivery module within ICD 14 to one or more of electrodes 24, 28, and 30, and transmit cardiac electrical signals developed across a pair of electrodes 24, 28, and 30 to a sensing module within ICD 14.

Defibrillation lead 16 is shown in FIG. 1 to include a defibrillation electrode 24, which may be an elongated coil electrode, along the distal portion of defibrillation lead 16. Defibrillation electrode 24 is located on lead 16 such that when ICD system 10 is implanted a therapy vector between defibrillation electrode 24 and housing 15 of ICD 14 is substantially through or across the ventricle(s) of heart 26.

Defibrillation lead 16 also includes one or more sensing electrodes 28 and 30, located toward the distal portion of defibrillation lead 16. Electrodes 28 and 30 are referred to herein as "sensing electrodes," however it is recognized that electrodes 28 and 30 may be used, together or in any combination with defibrillation electrode 24 or housing 50, to deliver pacing pulses. Likewise, while electrode 24 is referred to herein as a "defibrillation electrode," electrode 24 may be used as a pacing electrode, e.g., with housing 15 for delivering high energy pacing pulses such as post shock pacing pulses. In the example illustrated in FIG. 1, sensing electrodes 28 and 30 are separated from one another by defibrillation electrode 24. In other words, sensing electrode 28 is located distal to defibrillation electrode 24 and sensing electrode 30 is proximal to defibrillation electrode 24. In other embodiments, however, electrodes 28 and 30 may be located on the same side of defibrillation electrode 24 either distal or proximal to electrode 24. ICD system 10 may sense electrical activity of heart 26 via one or more sensing vectors that include combinations of electrodes 28 and 30 and the housing 15, sometimes referred to as a "can electrode," of ICD 14. For example, ICD 14 may receive a subcutaneous electrocardiogram (ECG) signal across a sensing vector between electrodes 28 and 30, a sensing vector between electrode 28 and the housing 15, a sensing vector between electrode 30 and housing 15, or any combination of electrodes 28 and 30 and housing 15. In some instances, ICD 14 may even sense cardiac electrical signals using a sensing vector that includes defibrillation electrode 24 and any one or more of electrodes 28 or 30 and housing 15.

ICD 14 analyzes the electrical signals received from one or more of the sensing vectors described above to detect and treat shockable tachyarrhythmias, such as VT or VF. ICD 14 may deliver one or more cardioversion or defibrillation shocks via defibrillation electrode 24 in response to detecting VT or VF. ICD 14 may also provide pacing therapy, such as anti-tachycardia pacing (ATP) in response to detecting a tachyarrhythmia and/or post-shock pacing after a cardioversion or defibrillation shock to treat post-shock asystole or bradycardia. After delivering a shock pulse or a high voltage pacing pulse using defibrillation electrode 24 and housing 15, a high amplitude polarization signal will occur and decay over time. As described herein, ICD 14 analyzes electrical signals received from one or more of the sensing vectors described above after delivery of a high energy therapeutic electrical stimulation pulse to identify intrinsic cardiac signals that are attendant to intrinsic cardiac events occurring during the post-stimulation polarization and are therefore superimposed on the polarization signal.

ICD 14 includes a housing 15 which forms a hermetic seal that protects internal electronic components of ICD 14. The housing 15 may be formed of a conductive material, such as titanium, titanium alloy, or other conductive material to serve as an electrode. Housing 15 may function as a "can electrode" since the conductive housing or a portion thereof may be coupled to internal circuitry to be used as an indifferent or ground electrode during sensing, pacing or cardioversion/defibrillation shock delivery. As will be described in further detail herein, housing 15 may enclose one or more processors, memory devices, transmitters, receivers, sensors, sensing circuitry, therapy circuitry and other appropriate components.

The example illustrated in FIG. 1 is illustrative in nature and should not be considered limiting of the techniques described in this disclosure. In other examples, ICD 14 and one or more associated leads may be implanted at other locations. For example, ICD 14 may be implanted in a subcutaneous pocket in the right chest. In this case, defibrillation lead 16 may extend subcutaneously from the device toward the manubrium of the sternum 22 and bend or turn and extend subcutaneously or substernally inferiorly from the manubrium of the sternum, substantially parallel with the sternum.

In another example, ICD 14 may be implanted subcutaneously outside the ribcage 32 in an anterior medial location. Lead 16 may be tunneled subcutaneously into a location adjacent to a portion of the latissimus dorsi muscle of patient 12, from a medial implant pocket of ICD 14 laterally and posteriorly to the patient's back to a location opposite heart 26 such that the heart 26 is generally disposed between the ICD 14 and distal defibrillation electrode 24 and distal sensing electrode 28.

The techniques disclosed herein may be implemented in numerous ICD or pacemaker and electrode configurations that include one or more housing-based electrodes and/or one or more lead-based electrodes for enabling sensing of a cardiac electrical signal developed across one or more sensing vectors and for delivering electrical stimulation therapies to heart 26 including shock pulses and/or pacing pulses. The IMD system 10 is an extravascular and extracardiac IMD system because lead 16 is positioned in an extravascular and extracardiac location outside the blood vessels, heart 26 and pericardium 38. It is understood that while ICD 14 and lead 16 may be positioned between the skin and a muscle layer of the patient 12, ICD 14 and any associated leads could be positioned in any extravascular and extracardiac location of the patient, such as below a muscle layer or even within the thoracic cavity but without direct contact with heart 26, e.g., in a substernal location.

Furthermore, the techniques disclosed herein may be implemented in an automatic external defibrillator (AED) that employs surface electrodes sensing cardiac signals and delivering therapy transcutaneously or in an ICD system that employs transvenous electrodes to deliver high energy CV/DF shock pulses and sensing of intrinsic cardiac events during the post-shock polarization signal is desired.

An external device 40 is shown in telemetric communication with ICD 14 by a communication link 42. Communication link 42 may be established between ICD 14 and external device 40 using a radio frequency (RF) link such as Bluetooth, Wi-Fi, or Medical Implant Communication Service (MICS) or other RF bandwidth. External device 40 may include a processor, display, user interface, and external telemetry unit and may be a programmer used in a hospital, clinic or physician's office to retrieve data from ICD 14 and to program operating parameters and algorithms in ICD 14 for controlling ICD 14 functions. External device 40 may alternatively be embodied as a home monitor or hand held device.

External device 40 may be used to program cardiac event sensing parameters such as parameters used to control sensing intrinsic R-waves during a post-shock or post-pace polarization signal. External device 40 may also be used to program ICD tachyarrhythmia detection parameters and therapy control parameters, including post-shock pacing control parameters and shock therapy control parameters.

Figure 3:
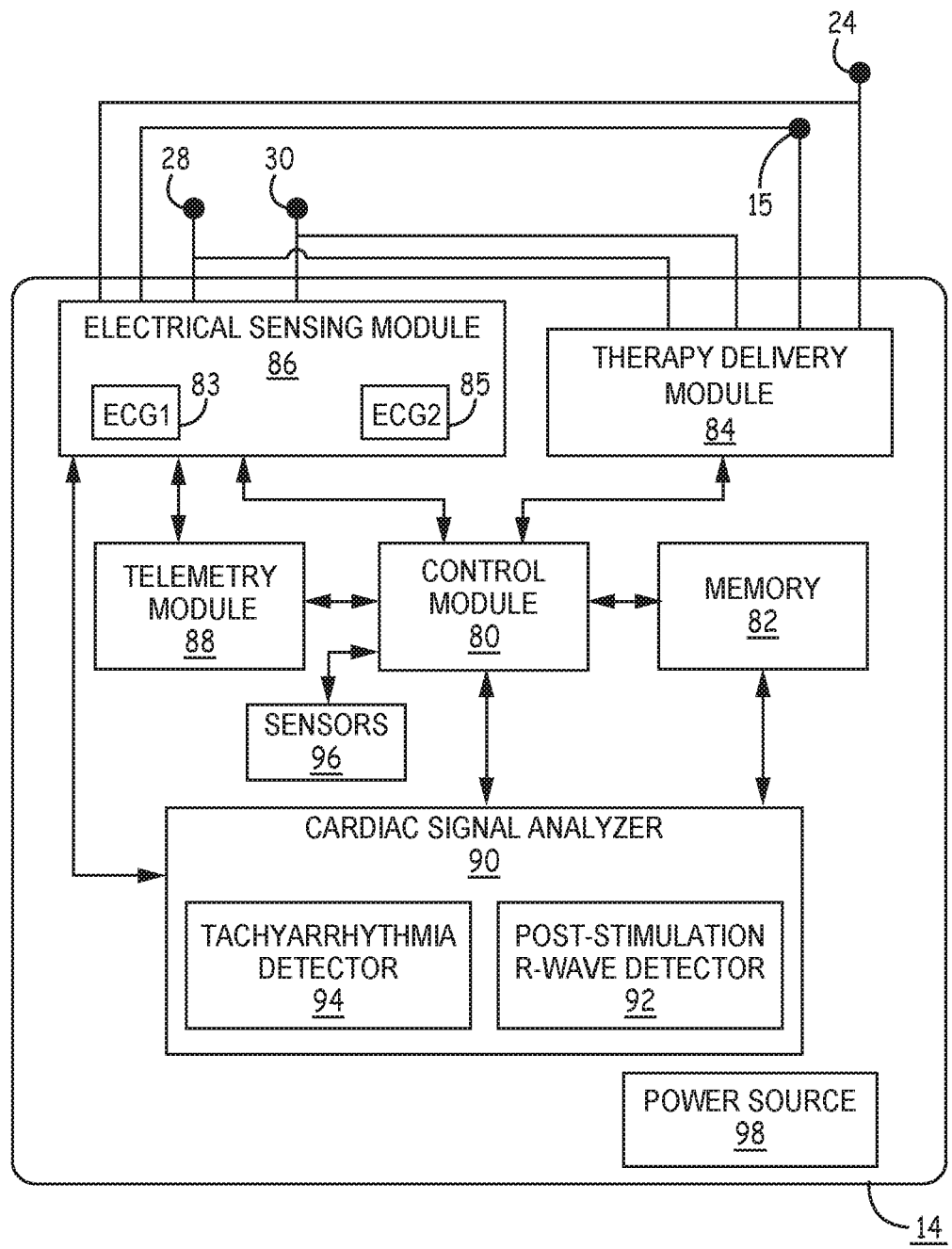
FIG. 3 is a schematic diagram of the ICD shown in FIG. 1 according to one example.

FIG. 3 is a schematic diagram of ICD 14 according to one example. The electronic circuitry enclosed within the housing of ICD 14 includes software, firmware and hardware that cooperatively monitor one or more ECG signals, determine when a CV/DF shock or pacing therapy is necessary, and deliver prescribed CV/DF and pacing therapies. In some examples, ICD 14 may be coupled to a lead, such as lead 16, carrying electrodes, such as electrodes 24, 28 and 30, positioned in operative relation to the patient's heart for delivering cardiac pacing pulses, including post-shock pacing, in addition to shock therapies. CV/DF shocks may be delivered using defibrillation electrode 24 and housing 15, represented in FIG. 3 as a return electrode. CV/DF shocks delivered transthoracically via defibrillation electrode 24 and housing 15 may typically be in the range of at least 10 Joules and up to 80 Joules. Extracardiac pacing pulses may be delivered, for example, using defibrillation electrode 24 and housing 15 having a pulse energy of at least approximately 1 mJ, e.g., between 20 mJ and 140 mJ. In contrast, typical cardiac pacing pulses delivered using endocardial electrodes may be on the order of 20 to 240 µJ.

ICD 14 and the associated techniques for sensing intrinsic cardiac events are described herein in conjunction with extracardiac electrodes 24, 28, 30 and housing 15 used to deliver high-energy stimulation pulses and sensing cardiac electrical signals. It is contemplated, however, that the disclosed techniques for sensing intrinsic events may be implemented in other ICD configurations that include transvenous leads carrying electrodes used to deliver high energy CV/DF shock pulses.

ICD 14 includes control module 80, memory 82, therapy delivery module 84, electrical sensing module 86, telemetry module 88, and cardiac signal analyzer 90. A power source 98 provides power to the circuitry of ICD 14, including each of the modules 80, 82, 84, 86, 88, and 90 as needed. Power source 98 may include one or more energy storage devices, such as one or more rechargeable or non-rechargeable batteries.

The functional blocks shown in FIG. 3 represent functionality that may be included in ICD 14 and implemented in any discrete and/or integrated electronic circuit components capable of producing the functions attributed to ICD 14 herein. As used herein, the term "module" refers to an application specific integrated circuit (ASIC), an electronic circuit, a processor (shared, dedicated, or group) and memory that execute one or more software or firmware programs, a combinational logic circuit, state machine, or other suitable components that provide the described functionality. The particular form of software, hardware and/or firmware employed to implement the functionality disclosed herein will be determined primarily by the particular system architecture employed in the device and by the particular detection and therapy delivery methodologies employed by the device. Providing software, hardware, and/or firmware to accomplish the described functionality in the context of any modern ICD, given the disclosure herein, is within the abilities of one of skill in the art.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common hardware or software components.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by a processor included in control module 80 or another module included in ICD 14, cause ICD 14 to perform various functions described herein. The non-transitory computer readable media storing the instructions may include any of the media listed above, with the sole exception being a transitory propagating signal.

Control module 80 communicates with therapy delivery module 84, cardiac signal analyzer 90 and electrical sensing module 86 for detecting cardiac rhythms and generating cardiac therapies as needed in response to sensed cardiac signals. Therapy delivery module 84 and electrical sensing module 86 are electrically coupled to electrodes 24, 28, and 30 carried by lead 16 (shown in FIG. 1) and housing 15, which may serve as a common or ground electrode.

Electrical sensing module 86 may be coupled to electrodes 28, 30 and housing 15 in order to monitor electrical activity of the patient's heart via one or more ECG sensing vectors. Electrical sensing module 86 may additionally be selectively coupled to electrode 24. For example, sensing module 86 may include switching circuitry for selecting which of electrodes 24, 28, 30 and housing 15 are coupled to sense amplifiers included in sensing module 86 used to sense cardiac electrical signals, such as R-waves for detecting arrhythmias. Switching circuitry may include a switch array, switch matrix, multiplexer, or any other type of switching device suitable to selectively couple sense amplifiers to selected electrodes.

In some examples, electrical sensing module 86 includes multiple sensing channels for sensing multiple ECG sensing vectors selected from electrodes 24, 28, 30 and housing 15. Sensing module 86 is shown to include two sensing channels 83 and 85 in the example of FIG. 3. Each sensing channel 83 and 85 may be configured to amplify and filter the ECG signal received from selected electrodes coupled to the respective sensing channel to improve the signal quality for sensing cardiac events, e.g., R-waves.

In one example, a first sensing channel 83 (ECG1) may be selectably configured to sense an ECG signal between sensing electrode 28 and ICD housing 15 and a second sensing channel 85 (ECG2) may be selectably configured to sense an ECG signal between sensing electrode 30 and ICD housing 15. In another example, one sensing channel 83 or 85 may receive an ECG signal using electrodes 28 and 30 and the other sensing channel 83 or 85 may receive an ECG signal using one of electrodes 28 and 30 paired with the housing 15.

Each sensing channel 83 and 85 may include cardiac event detection circuitry for sensing cardiac event signals from the received ECG signal developed across the selected electrodes 24, 28, 30 or 15. Cardiac event sensing thresholds used by each sensing channel 83 and 85 may be automatically adjusted according to sensing control parameters, which may be stored in memory 82. Control of the automatically-adjusted cardiac event sensing threshold for each sensing channel 83 and 85 may be implemented in control module 80, sensing module 86 or a combination of both. A given sensing channel 83 and 85 senses a cardiac event when the respective received ECG signal crosses auto-adjusting cardiac event sensing threshold outside a blanking interval. A sensed event signal, e.g., an R-wave sensed event signal, is produced when the ECG signal crosses the threshold. The R-wave sensed event signal is passed to control module 80 for use in controlling the timing of electrical stimulation pulses delivered by therapy delivery module 84.

Sensing module 86 may include an analog-to-digital converter for providing a digital ECG signal from one or both ECG sensing channels 83 and 85 to cardiac signal analyzer 90. For example each ECG signal received by channels 83 and 85 may be converted to a multi-bit digital signal by sensing module 86 and provided to cardiac signal analyzer 90 for signal analysis. Cardiac signal analyzer 90 may include a tachyarrhythmia detector 94 for detecting and discriminating shockable and non-shockable rhythms by analysis of the ECG signal(s). Results of analysis performed by tachyarrhythmia detector 94 may be used by control module 80 in combination with R-wave sense event signals received from electrical sensing module 86 for detecting tachyarrhythmia and controlling therapy delivery module 84.

Examples of algorithms that may be performed by ICD 14 for detecting, discriminating and treating shockable rhythms are generally disclosed in U.S. Pat. No. 5,354,316 (Keimel); U.S. Pat. No. 5,545,186 (Olson, et al.); U.S. Pat. No. 6,393,316 (Gillberg et al.); U.S. Pat. No. 7,031,771 (Brown, et al.); U.S. Pat. No. 8,160,684 (Ghanem, et al.), U.S. Pat. No. 8,301,233 (Zhang et al.), and U.S. Pat. No. 8,437,842 (Zhang, et al.), all of which patents are incorporated herein by reference in their entirety. The detection algorithms are highly sensitive and specific for the presence or absence of life threatening, shockable VT and VF. It should be noted that implemented arrhythmia detection algorithms may utilize not only ECG signal analysis methods but may also utilize supplemental sensors 96, such as blood pressure, tissue oxygenation, respiration, patient activity, heart sounds, and the like, for contributing to a decision by processing and control module 80 to apply or withhold a therapy.

In response to detecting a shockable tachyarrhythmia, control module 80 controls therapy delivery module 84 to deliver a CV/DF shock pulse. Therapy delivery module 84 includes a high voltage (HV) therapy delivery module including one or more HV output capacitors for delivering HV CV/DF shock pulses. When a malignant tachycardia is detected, the HV capacitors are charged to a pre-programmed voltage level by a HV charging circuit. HV CV/DF shock pulses may be delivered with a pulse energy of approximately 10 J to 80 J in some examples.

Control module 80 applies a signal to trigger discharge of the HV capacitors upon detecting a feedback signal from therapy delivery module 84 that the HV capacitors have reached the voltage required to deliver a programmed shock energy. In this way, control module 80 controls operation of the high voltage output circuit of therapy delivery module 84 to deliver high energy CV/DF shocks using defibrillation electrode 24 and housing 15.

After a CV/DF shock, post-shock pacing pulses may be required to treat asystole or bradycardia during shock recovery using extracardiac electrodes coupled to ICD 14. Therapy delivery module 84 may also be configured for generating and delivering cardiac pacing pulses, e.g., transthoracic pacing pulses delivered using extracardiac electrodes carried by lead 16 for treating post-shock asystole, and/or for delivering tachyarrhythmia induction pulses delivered to induce VT or VF during ICD testing. High energy extracardiac pacing pulses may be delivered having a pulse energy ranging from approximately 20 mJ to 140 mJ. Depending on the location of the extracardiac electrodes, e.g., intrathoracic vs. extrathoracic, the pulse energy of extracardiac pacing pulses may be higher or lower than this approximate range but are expected to be on the order of mJ, e.g., at least 1 mJ or higher.

Cardiac signal analyzer 90 further includes a post-stimulation R-wave detector 92. ECG signal analysis is performed by post-stimulation R-wave detector 92 to detect intrinsic activity during the polarization signal that follows a CV/DF shock or a pacing pulse so that control module 80 is not blinded to intrinsic cardiac signals during the polarization signal. Control module 80 includes a timing circuit comprising various timers and/or counters for measuring time intervals, such as RR intervals between sensed R-waves and for setting pacing escape intervals for controlling pacing pulses delivered by therapy delivery module 84 when an R-wave is not sensed prior to expiration of the pacing escape interval.

Post-stimulation R-wave detector 92 analyzes electrical signals sensed using extracardiac electrodes to detect R-waves superimposed on or occurring during the post-stimulation polarization caused by delivering high-energy stimulation pulses, CV/DF shocks and/or pacing pulses. If an intrinsic R-wave signal is detected during the polarization signal by post-stimulation R-wave detector 92, cardiac signal analyzer 90 may pass a sensed event signal to control module 80. A sensed event signal received during a pacing escape interval set by control module 80 may be used to reset the escape interval without delivering a scheduled pacing pulse. In this way, intrinsic activity sensed during a prolonged high-amplitude polarization signal can be used to inhibit a pacing pulse to allow intrinsic heart activity to control the heart rhythm, e.g., after delivery of a shock pulse.

Therapy delivery module 84 may be configured to deliver relatively high-energy pacing pulses, e.g., up to 40 volts or higher in voltage amplitude or up to 200 milliamps or higher, to provide subcutaneously delivered transthoracic pacing pulses. Therapy delivery module 84 may programmed to deliver extracardiac pacing pulses having a pulse width between 5 ms and 10 ms. For example, with no imitation intended extracardiac post-shock pacing pulses may be delivered as biphasic, 200 mA pulses having a pulse voltage amplitude between approximately 5 and 40 Volts and a pulse width between 5 and 10 ms for treating post-shock asystole. User-programmable therapy control parameters may be programmed into memory 82 via telemetry module 88.

Telemetry module 88 includes a transceiver and antenna for communicating with external device 40 (shown in FIG. 1) using RF communication. Under the control of control module 80, telemetry module 88 may receive downlink telemetry from and send uplink telemetry to external device 40. ECG episode data related to the detection of a shockable rhythm and the delivery of a CV/DF shock may be stored in memory 82 and transmitted by telemetry module 88 to external device 40 upon receipt of an interrogation command. Clinician review of episode data facilitates diagnosis and prognosis of the patient's cardiac state and therapy management decisions, including selecting programmable control parameters used for detecting shockable rhythms, sensing cardiac signals, and delivering therapy.

Figure 4:
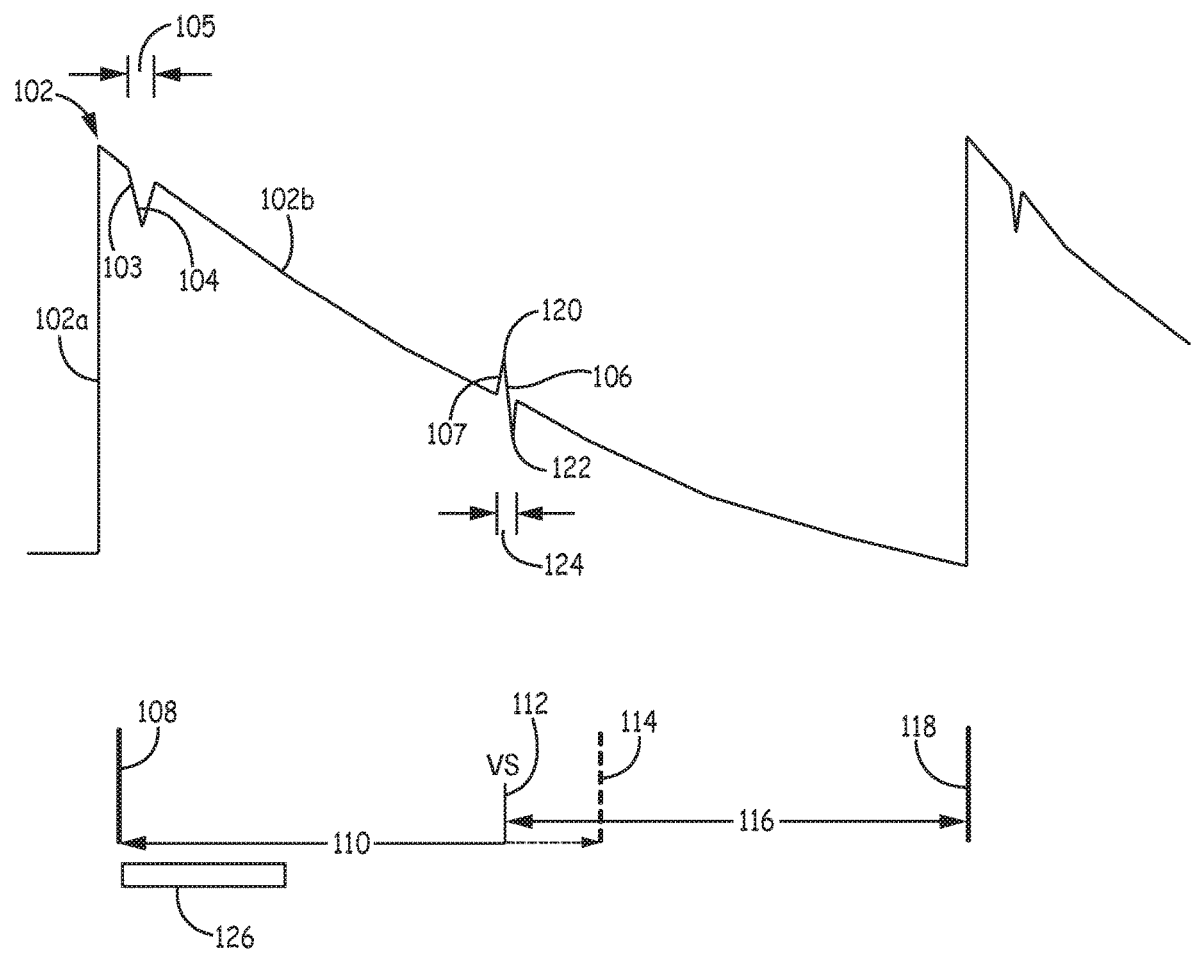
FIG. 4 is an illustration of a pace polarization signal during which an evoked R-wave and intrinsic R-wave occur.

FIG. 4 is a depiction of a post-stimulation polarization signal 102 during which an evoked response R-wave 104 and an intrinsic R-wave 106 occur. The polarization signal 102 includes a sharply rising portion 102a upon delivery of an electrical stimulation pulse 108 followed by a decaying portion 102b. Stimulation pulse 108 is a high energy pulse, e.g., a transthoracic shock or pacing pulse delivered by ICD 14 using extracardiac electrodes carried by lead 16. In the case of stimulation pulse 108 being a CV/DF shock, sensing of intrinsic cardiac events may be performed during polarization signal 102 for verifying success of the shock in cardioverting or defibrillating the heart, for early redetection of the tachyarrhythmia if the shock did not succeed, and for determining a need for post-shock pacing. In the example shown, stimulation pulse 108 is a pacing pulse, followed by an evoked response signal 104. In the case of stimulation pulse 108 being a pacing pulse, a sensing of intrinsic R-wave 106 is used to inhibit the next pacing pulse.

A pacing escape interval 110 may be set upon delivery of the stimulation pulse 108 to control post-shock pacing. The polarization signal 102 is large in amplitude and the decaying portion 102b may not return to baseline for a relatively long period of time, e.g., for more than 500 ms, which may be a majority of or more than one pacing escape interval 110. In the example shown, the polarization signal 102 extends for more than one pacing escape interval 110.

Sensing of intrinsic R-waves by a threshold-based cardiac event detector included in electrical sensing module 86 during escape interval 110 is impaired due to the high amplitude of polarization signal 102. The amplitude of signal 102 may be much greater than the amplitude of intrinsic R-waves and greater than an R-wave sensing threshold used by sensing module 86 for detecting R-waves from the ECG signal when no polarization artifact is present. As a result, sensing module 86 may conceivably sense an ECG signal amplitude greater than the R-wave sensing threshold throughout a pacing escape interval 110, masking the presence of an intrinsic R-wave 106 that is superimposed on the polarization signal 102.

In some examples, cardiac signal analyzer 90 may monitor for an evoked response signal 104 following stimulation pulse 108 to verify that the pulse 108 has captured the heart. A method and apparatus for detecting an evoked response following a pacing pulse during a pace polarization signal is generally disclosed in U.S. Pat. No. 6,134,473 (Hemming, et al.), incorporated herein by reference in its entirety. The polarization signal following a relatively low energy pacing pulse, e.g., 5 Volts or less, delivered using endocardial electrodes decays relatively quickly. The evoked response signal following the low energy pacing pulse may occur during the polarization signal, but interference of the post-pace polarization signal with intrinsic R-wave sensing disappears quickly following low energy pacing pulses and can be further minimized using low polarization electrodes. Sensing intrinsic R-waves following low energy pacing pulses, therefore, typically does not require special techniques since reliable sensing by a sense amplifier using an auto-adjusted sensing threshold is restored relatively soon after the low energy pacing pulse. In contrast, the large amplitude long duration polarization signal 102 caused by the high energy stimulation pulse 108 will impair sensing of intrinsic R-wave 106 based on an R-wave sensing threshold by electrical sensing module 86 for a relatively long period of time. The techniques disclosed herein enable sensing of the intrinsic R-wave 106 during the polarization signal 102 and discrimination of the intrinsic R-wave 106 from the evoked response signal 104 (when it occurs).

As described below, cardiac signal analyzer 90 of ICD 14 is configured to sense the intrinsic R-wave 106 during the polarization signal 102, when the sensing function of electrical sensing module 86 may be impaired by the polarization signal 102. Post-stimulation R-wave detector 92 may detect cardiac electrical signals during post-stimulation polarization signal 102 based on an accelerated slope 103 of the decaying portion 102b or a reversed polarity slope 107 of decaying portion 102b. As described below in conjunction with FIGS. 5 and 6, post-stimulation R-wave detector 92 identifies intrinsic R-wave 106 based on features that differentiate it from evoked response signal 104.

In some examples, a sensing delay interval 126 is applied after the stimulation pulse 108 to allow time for the polarization signal 102 to decay. If stimulation pulse 108 is a shock pulse, polarization signal 102 may have a very large amplitude that is out of range of the post-stimulation R-wave detector 92. A sensing delay interval 126 may be used to allow polarization signal 102 to come back into a sensing range.

Upon identifying intrinsic R-wave 106, cardiac signal analyzer 90 produces an R-wave sense event signal 112 (labeled "VS" in FIG. 4), which causes control module 80 to terminate ventricular pacing escape interval 110, which was started upon delivery of stimulation pulse 108. A pacing pulse 114 scheduled for delivery upon expiration of pacing escape interval 110 is withheld. Control module 80 restarts a new ventricular pacing escape interval 116 upon the VS event signal 112. If a VS signal is not received by control module 80 during escape interval 116, a pacing pulse 118 is delivered upon expiration of escape interval 116, resulting in another polarization signal. Cardiac signal analyzer 90 may continue to detect intrinsic R-waves during the next polarization signal.

Characteristics of R-wave 106 that differentiate it from the pacing evoked response signal 104 are used to positively identify intrinsic R-wave 106 during polarization signal 102. For example, since the myocardial depolarization wavefront associated with intrinsic R-wave 106 travels toward a sensing electrode (e.g., electrode 28 or 30) then away from the sensing electrode, R-wave 106 is typically a biphasic signal having a positive-going peak 120 followed by a negative-going peak 122 (or a negative-going peak followed by a positive-going peak). The evoked depolarization caused by stimulation pulse 108 is traveling through the myocardial tissue away from the pacing electrode. Evoked response signal 104 will therefore typically be monophasic, having a single, negative-going, peak as illustrated in FIG. 4. The biphasic intrinsic R-wave 106 will typically have a narrower signal width 124 than the signal width 105 of the monophasic evoked response signal 104 due to the specialized conduction pathways that conduct the intrinsic depolarization.

Since the intrinsic R-wave 106 will typically occur later in time after a stimulation pulse 108 than the evoked response signal 104, timing relative to a stimulation pulse 108 may be used to differentiate the evoked response signal 104 from an intrinsic R-wave 106 in some cases. For instance, if a cardiac electrical signal is detected on the polarization signal 102 later than a time interval threshold after the stimulation pulse 108, for example later than approximately 200 ms after the stimulation pulse 108, the detected cardiac signal may be presumed to be an intrinsic R-wave 106 and not an evoked response signal 104.

However, the intrinsic R-wave 106 may not always arrive at a distinctly different time than the evoked response 104. Fusion beats are beats in which the timing of the stimulation pulse 108 results in fusion of the evoked response 104 and the intrinsic R-wave 106. It may be desirable to detect a fusion beat as intrinsic activity during a pacing escape interval to inhibit pacing pulses, e.g., during post-shock pacing to enable recovery of the intrinsic heart rhythm post-shock. Since the evoked response signal and the intrinsic R-wave signal are merged, the fusion beat signal will include characteristics of the R-wave 106, such as two signal peaks having differing polarities, which differentiate the fusion beat from a pure evoked response. For the purposes of sensing intrinsic activity to withhold pacing, the fusion beat may be detected as an intrinsic R-wave, and an R-wave sense event signal may be produced by cardiac signal analyzer 90 to cause control module 80 to reset the currently running pacing escape interval.

Figure 5:
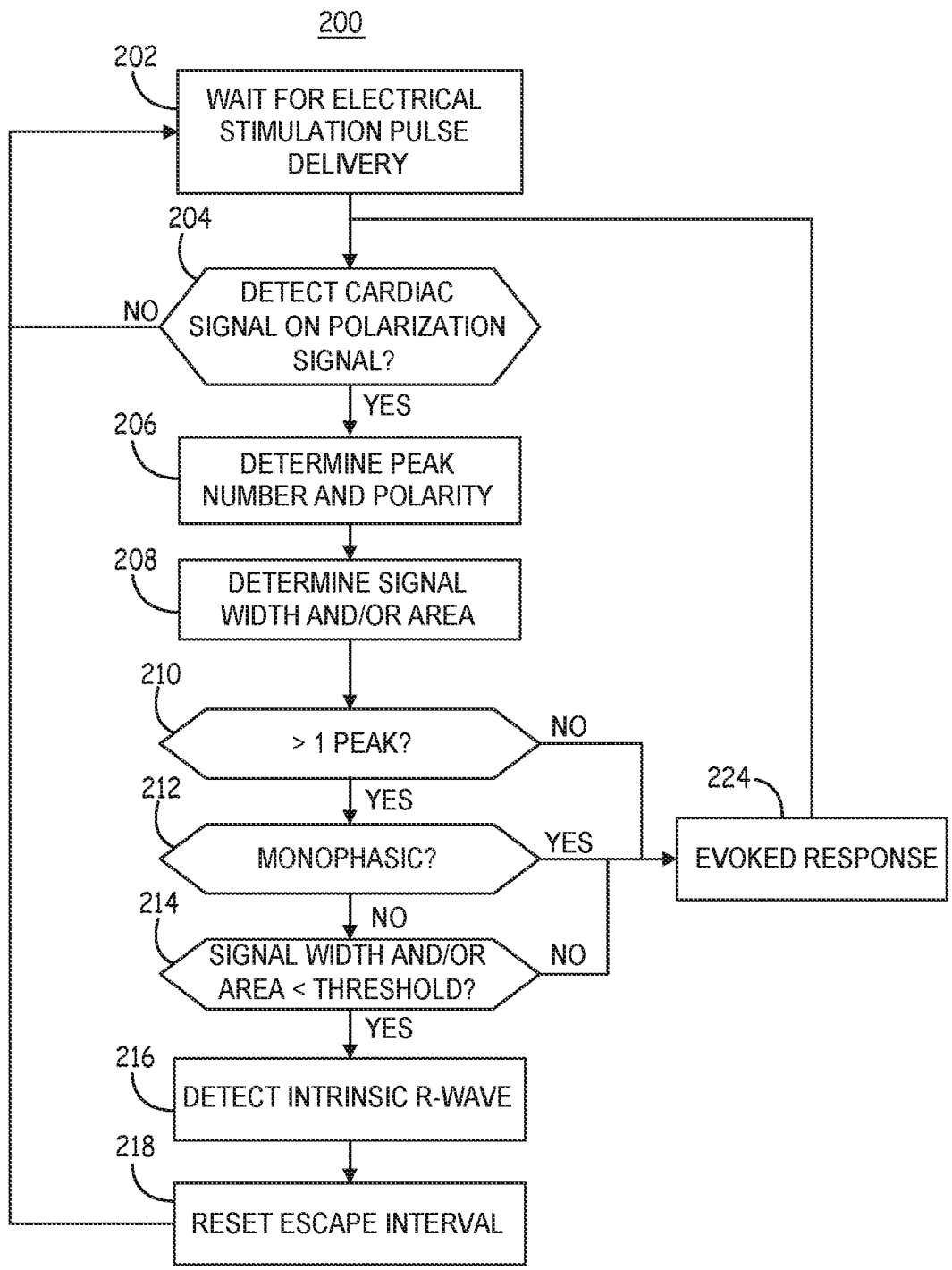
FIG. 5 is a flow chart of a method for detecting intrinsic cardiac signals during a post-stimulation polarization signal.

FIG. 5 is a flow chart 200 of a method for detecting intrinsic cardiac signals during a post-stimulation polarization signal. At block 202, the cardiac signal analyzer 90 waits for an electrical stimulation pulse delivery, which may be a CV/DF shock or a pacing pulse. Upon stimulation pulse delivery, the electrical sensing module 86 may be enabled by control module 80 to pass an ECG signal from one or both sensing channels 83 and 85 to cardiac signal analyzer 90 for detecting intrinsic cardiac signals during the post-stimulation polarization signal. One or both ECG signals may be analyzed by post-stimulation R-wave detector 92 for detecting an R-wave during the polarization signal.

In system 10 shown in FIGS. 1 and 3, ECG1 83 may be received across electrode 28 and housing 15, and ECG2 85 may be received across electrode 30 and housing 15. In other examples, ECG1 83 may be received between the defibrillation electrode 24 and the housing 15, and ECG2 85 may be received between one of sensing electrodes 28 and 30. The vertical sensing vector between electrodes 28 and 30, however, may be inferior for sensing R-waves due to lower ECG R-wave amplitude compared to a relatively more transverse vector between one of electrodes 24, 28, 30 and housing 15. Using the techniques disclosed herein, a vector that includes housing 15 and/or defibrillation electrode 24 may be used for sensing intrinsic events after the stimulation pulse, even when the stimulation pulse is delivered using housing 15 and defibrillation electrode 24. Switching to a different sensing vector that excludes both electrodes 15 and 24 used to deliver a stimulation pulse in order to avoid polarization signal interference may be unnecessary using the presently disclosed techniques. Sensing an ECG signal using a relatively more transverse vector that has a relatively higher R-wave amplitude, e.g., a vector that employs housing 15 rather than the vertical vector between electrodes 18 and 30, may be particularly useful during post-stimulation sensing when detecting of intrinsic activity is important for appropriately controlling ICD functions.

For each ECG signal received, post-stimulation R-wave detector 92 tracks the post-stimulation polarization signal, such as signal 102 of FIG. 4, to detect a cardiac signal superimposed on the polarization signal at block 204. In one example, the post-stimulation R-wave detector 92 includes a peak tracking circuit that detects a change in polarity of the polarization signal or detects a change in slope of the polarization signal, e.g., an acceleration of a negative slope of the polarization signal 102 or a reversal of the polarity of the slope. The slope of the decaying portion of the polarization signal 102 is not expected to suddenly increase or change direction. Either of these slope changes can be used at block 204 to detect a cardiac electrical signal, evoked or intrinsic, superimposed on the polarization signal 102.

These slope changes of the decaying portion 102b of the polarization signal 102 that are evidence of a cardiac electrical signal superimposed on the polarization signal 102 can be observed in FIG. 4. For example, the negative-going peak of evoked response 104 is preceded by an accelerated negative slope 103 along the decaying portion 102b of the polarization signal 102. In the case of the intrinsic R-wave 106, the slope of the decaying portion 102b switches in polarity from a negative slope to a positive slope 107 that rises to positive-going peak 120. If the intrinsic R-wave 106 is characterized by a biphasic signal having a negative-going peak first followed by a positive-going peak, the negative slope of the decaying portion 102b of polarization signal 102 will accelerate to the leading negative peak, similar to the situation of evoked response 104, then be followed by the change in slope polarity to a positive slope leading to a positive-going peak.

Thus an acceleration of the negative slope of the decaying portion 102b of polarization signal 102 and/or a change in the polarity of the slope can be used to detect the presence of a cardiac electrical signal superimposed on polarization signal 102. Circuitry included in post-stimulation R-wave detector 92 for detecting a cardiac electrical signal superimposed on the polarization signal 102 may correspond generally to circuitry disclosed in the above-incorporated '473 patent (Hemming, et al.) for detecting an evoked response during a post-pace polarization signal.

If a cardiac electrical signal is not detected during the polarization signal, the post-stimulation R-wave detector 92 returns to block 202 to wait for the next electrical stimulation pulse delivery. Post-stimulation R-wave detector 92 may be enabled to continue searching for a cardiac signal by monitoring for a change in the slope of decaying portion 102b until the next stimulation pulse or until an intrinsic R-wave is sensed. In practice, a back-up pacing pulse may be scheduled when an evoked response signal is not detected within a predetermined time interval, e.g., 50 ms, following a pacing pulse. If a cardiac signal is not detected at block 204 within the predetermined time interval, a back-up pulse may be delivered immediately in which case the next stimulation pulse may come relatively soon at block 202, sometimes with a higher energy (higher amplitude and/or pulse width).

If a cardiac electrical signal is detected at block 204, additional signal features may be determined by post-stimulation R-wave detector 92 in order to discriminate intrinsic R-waves from evoked R-waves. For example, after detecting a cardiac electrical signal based on a slope change of the decaying portion 102b, the peak tracking circuit of post-stimulation R-wave detector 92 may determine how many peaks the detected superimposed cardiac signal has and the polarity of each detected peak relative to the polarity signal 102 at block 206. Peaks may be identified based on a change in sign of the amplitude difference determined between signal sample points that occur a predetermined time interval apart, e.g., 20 ms apart or less. Alternatively, peaks could be identified by setting a threshold greater than the polarization signal and a threshold less than the polarization signal at a given point in time such that if a threshold is crossed a peak is counted. Once one threshold is crossed resulting in the first peak being counted, e.g., a positive going peak, the next peak is counted only after the opposite threshold is crossed, e.g., a negative-going peak. The peak tracking circuit of post-stimulation R-wave detector 92 may be configured to detect peaks within a time window of detecting the cardiac electrical signal, e.g., 100 ms or less. Alternatively the peak tracking circuit may detect a return to the expected slope of the decaying portion 102b of polarization signal 102 and stop searching for peaks of the detected cardiac signal.

At block 208, the post-stimulation R-wave detector 92 may determine a width of the detected cardiac signal. For example, the signal width may be determined as the time from detection of the cardiac electrical signal (based on the change in the polarity of the slope or the steepness of the slope of the decaying portion 102b) until a return to the expected slope of the decaying portion 102b. An expected slope of the decaying portion 102b may be based on a predefined slope threshold that is expected to always be less than the slope 103 of an evoked response signal 102 and the slope 107 of an R-wave 106. Alternatively, the slope of the polarization signal may be measured when a cardiac signal is not being detected and used to establish an expected slope or slope range of the decaying portion 120b. The signal width 105 or 124 may be determined as the time from the onset of detecting the cardiac signal (evoked response signal 104 or intrinsic R-wave 106) until the expected slope is detected again.

Determination of the expected slope of polarization signal 102 in the absence of a cardiac signal could be performed by regional modelling of the exponential polarization decay. Absence of a cardiac signal may be inferred from a lack of slope disturbance, i.e., no change in polarity of the slope or acceleration of the slope.

In another example, the signal onset is determined as a time point that the slope of the decaying portion 102b changes from a slow slope to a fast slope. The slope may be determined between two sample points at predetermined time intervals apart, e.g., 20 ms apart. The difference between two consecutively determined slopes may be compared to a difference threshold. If the difference exceeds the threshold, a large change in the slope is detected as the onset of the signal. In a similar manner, the end of the signal may be detected as a time point that the slope changes back from a fast slope to a slow slope, e.g., by determining that the difference between two consecutively determined slopes is less than a difference threshold. The signal width is the time interval from the detected onset to the detected end point.

In yet another example, the signal width may be determined at a predetermined fraction of the peak amplitude. For example, the time interval between a signal sample point at 50% of the peak amplitude prior to the peak and a signal sample point at 50% of the peak amplitude after the peak may be determined as the signal width.

Instead of determining signal width at block 208, or in addition to, the signal area may be determined at block 208. The signal width and consequently signal area of the intrinsic R-wave is expected to be less than the signal width and signal area of the evoked response signal. Signal area may be determined as the sum of the absolute values of the samples points during the detected signal (based on determining an onset and end as described above). Signal area may be determined as the signed area where sample points greater than a mean amplitude of the detected signal are positive terms and sample points less than the mean amplitude of the detected signal are negative terms. The negative summation of the negative terms is subtracted from the positive summation of the positive terms yielding a signed signal area.

At blocks 210 through 214, one or more features of the detected cardiac signal may be compared to criteria that differentiate the intrinsic R-wave 106 from the evoked response signal 104. For example, the number of signal peaks determined at block 206 may be used to determine whether the detected cardiac signal is an evoked response or an intrinsic R-wave. More than one signal peak supports the decision that the detected cardiac signal is an intrinsic R-wave at block 216. If only a single peak is detected as determined at block 210, the detected cardiac signal is determined to be the evoked response signal 104 at block 224. The process may return to block 204 to detect another cardiac electrical signal during the polarization signal 102. If no additional superimposed cardiac electrical signal is detected during the decaying portion 102b, the ECG signal(s) received after the next electrical stimulation pulse is delivered at block 202 is(are) analyzed at block 204.

If more than one signal peak is detected at block 210, the post-stimulation R-wave detector 92 may determine whether the detected signal is at least biphasic based on at least one signal peak being negative-going relative to the polarization signal 102 and at least one signal peak being positive going relative to the polarization signal 102. Both signal peaks, e.g., peaks 120 and 122, may have a positive amplitude, but one peak 120 follows a positive-going slope while the other peak 124 follows a negative-going slope. Two peaks or more detected within the detected cardiac signal that follow slopes of the same polarity may not be detected as an intrinsic cardiac signal since the signal may be a monophasic signal relative to the polarization signal 102 having multiple peaks of the same polarity. An evoked response signal 104 could have a double peak in the same direction in some instances, e.g., a negative-going slope reaching a first negative peak, a brief flat or positive-going slope, then another negative-going slope followed by a second negative peak. In order to verify that the detected cardiac signal is an intrinsic R-wave, the detected cardiac signal must be at least biphasic having at least one peak following a positive-going slope and one peak following a negative-going slope need to be detected in some embodiments. If the signal is monophasic, as determined at block 212, the detected signal may be identified as evoked response signal 104 at block 224.

If the detected cardiac signal is not monophasic (e.g., biphasic, triphasic, etc.) at block 212, the signal width and/or area determined at block 208 may be compared to a respective signal width threshold or area threshold at block 214. In various examples, the signal width threshold is a predetermined threshold or a threshold set based on a previous signal width measurement of a known evoked response signal or a known intrinsic signal. The signal width threshold may be set to a percentage of the known evoked response signal width 105 (shown in FIG. 4), e.g., 70% of signal width 105. Similarly, a signal area threshold may be set based on the area determined for a previously detected known evoked response signal or intrinsic signal, In other examples, if the evoked response signal 104 (FIG. 4) has been identified after the most recent electrical stimulation pulse 108 and prior to the currently detected but still unknown cardiac electrical signal 106, the signal width 124 of the currently unknown detected cardiac signal 106 may be compared to the signal width 105 of the identified evoked response signal 104. If the signal width 124 is less than a predetermined signal width threshold, or less a preceding detected evoked response signal width 105, the unknown signal 106 is identified to be an intrinsic R-wave 106 at block 216.

In FIG. 5, all of decision blocks 210, 212 and 214 are performed in order to identify a detected cardiac signal as an intrinsic cardiac signal at block 106 or an evoked response 104 at block 224. In various examples, however, all of blocks 210, 212 and 214 may not be required. One or more of the criteria shown in the decision blocks 210, 212 and 214 may be used for identifying a detected cardiac signal superimposed on the polarization signal 102 as an evoked response 104 or an intrinsic cardiac signal 106. If a detected cardiac signal is identified as an evoked response signal at block 224 and another cardiac signal is detected during the same polarization signal after the evoked response signal, the next cardiac signal may be identified as an intrinsic R-wave based on the knowledge that an evoked response signal has already been detected. Alternatively, less stringent criteria may be applied to identify an intrinsic R-wave if an evoked response signal has already been identified, e.g., only verifying at least two peaks of opposite polarity relative to the polarization signal 102 without determining signal width.

The criteria applied to discriminate the intrinsic R-wave 106 from the evoked response signal 104 and the polarization signal 102 may be established for a particular ICD 14 (or other device employing the techniques disclosed herein) taking into account the behavior of the polarization signal 102, evoked response signal 104, and intrinsic R-wave 106 when filtered by the particular input filter properties of the ICD 14. Criteria relating to the number of signal peaks, the signal width and the signal area may differ between different hardware applications depending in part on the filtering of the ECG signal.

If an intrinsic R-wave is detected at block 216, the pacing escape interval started upon delivery of the pacing pulse delivered at block 202 is reset at block 218 by control module 80 such that the next scheduled pacing pulse is inhibited. The process returns to block 202 to wait for the next electrical stimulation pulse. It is recognized that in some cases, a second intrinsic event may occur during the same polarization signal if the post-stimulation polarization signal is relatively long, e.g., greater than 500 ms and/or the intrinsic heart rhythm is fast due to sinus or non-sinus tachycardia. As such, after resetting the escape interval, the ongoing decaying polarization signal 102 may be analyzed for detecting another intrinsic cardiac signal. Additional intrinsic cardiac signals identified during the polarization signal 102 may be used by control module 80 for resetting the pacing escape interval as well as for tachyarrhythmia detection by tachyarrhythmia detector 94.

Figure 6:
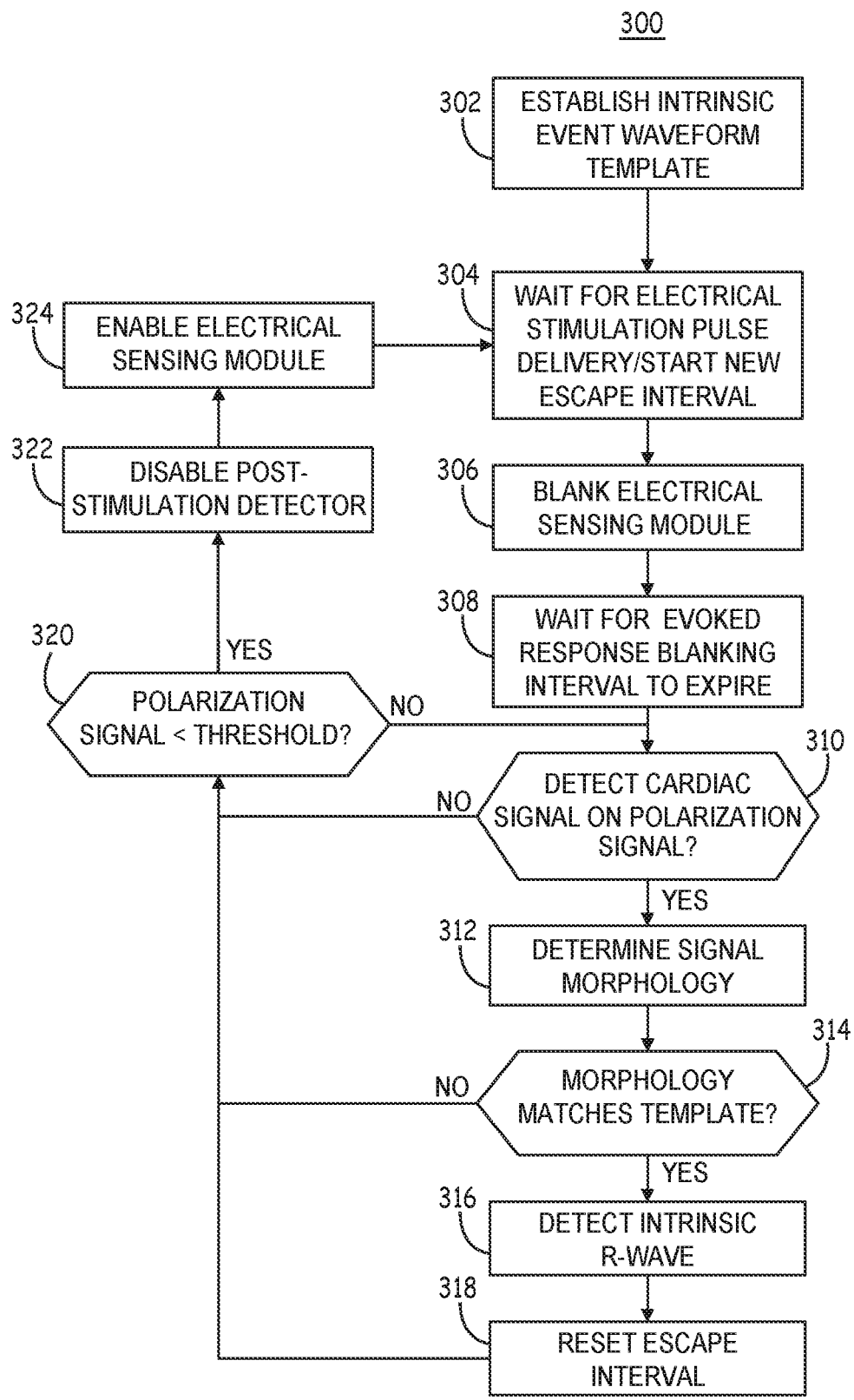
FIG. 6 is a flow chart of a method for sensing intrinsic cardiac activity during a post-stimulation polarization signal according to another example.

FIG. 6 is a flow chart 300 of a method for sensing intrinsic cardiac activity during a post-stimulation polarization signal according to another example. At block 302, an intrinsic cardiac signal waveform template is established. This template may be based on a waveform transformation of the ECG signal during a polarization signal or when a known intrinsic event occurs outside of the polarization signal (e.g., before a stimulation pulse or after full decay of the post-stimulation polarization signal). A wavelet transformation of the ECG signal may be performed to generate a template of the intrinsic R-wave waveform shape in some examples. The template may be generated from an R-wave signal or an average of multiple R-wave signals.

At block 304, the cardiac signal analyzer 90 waits for an electrical stimulation pulse delivered by therapy delivery module 84. A pacing escape interval may be started by control module 80 upon delivery of the stimulation pulse. After the stimulation pulse, the control module 80 may disable sensing of intrinsic events by electrical sensing module 86 during the post-stimulation polarization signal at block 306. The sensing module 86 may be disabled by setting a blanking period during which sense amplifiers are disabled in electrical sensing module 86 that become saturated by the polarization signal and are not the amplifiers used to provide an ECG signal to post-stimulation R-wave detector 92. In some examples, one or more sensing channels may be included in electrical sensing module 86 that pass ECG signals to post-stimulation R-wave detector 92. These sensing channels may remain enabled during the polarization signal, whereas the one or more sensing channels of sensing module 86 that are used for sensing R-waves based on an auto-adjusted sensing threshold amplitude when a polarization signal is not present may be blanked during the post-stimulation polarization signal. For instance, the sense amplifiers for those channels may be powered down while continuing to provide power to the sensing channel(s) that provide an ECG signal to post-stimulation R-wave detector 92.

Alternatively, cardiac event sensing by sensing module 86 is disabled during a blanking period by ignoring sense event signals produced by sensing module 86 during the polarization signal. The blanking period applied to sensing module 86 at block 306 may be a predetermined time interval expected to encompass a portion of the post-stimulation polarization signal 102 after which the sensing module 86 is expected to reliably sense cardiac signals, e.g., based on an auto-adjusted sensing threshold that decays after each sensed event.

In other examples, the blanking period is terminated by the control module 80 after the polarization signal 102 has reached a predetermined threshold. The predetermined threshold may be a programmed nominal threshold or a threshold set by control module 80. Electrical sensing module 86 may set an auto-adjusted R-wave sensing threshold to a percentage of the peak amplitude of the most recently sensed R-wave, e.g., 60% of the previous R-wave peak amplitude. The period of time that electrical sensing module 86 is blanked or disabled at block 306 may be until the polarization signal amplitude falls below the current auto-adjusted R-wave sensing threshold set by electrical sensing module 86.

At block 308, the post-stimulation R-wave detector 92 may be configured to wait for an evoked response blanking interval (which may be set by control module 80). An evoked response blanking interval may optionally be applied for a fixed interval of time after the stimulation pulse 108 is delivered to avoid detection of the evoked response signal 104 during the polarization signal decaying portion 102b. A peak tracking circuit of post-stimulation R-wave detector 92 may not be enabled to detect a cardiac signal at block 310 until after the evoked response blanking interval has expired. In this way, the evoked response signal 104 and the intrinsic R-wave 106 can be discriminated based on time of occurrence after the stimulation pulse 108. Fusion beats that occur during the evoked response blanking interval, however, may be missed.

After the evoked response blanking interval, a cardiac signal superimposed on the polarization signal 102 is detected by post-stimulation R-wave detector 92 as described previously in conjunction with FIG. 5. Upon detecting a superimposed cardiac signal, the morphology of the detected cardiac signal waveform is determined at block 312, using the same transformation technique used to generate an intrinsic waveform signal template. At block 314, the morphology of the detected signal is compared to the previously established template to determine a correlation metric. If the detected signal waveform matches the template e.g., based on the correlation metric exceeding a correlation threshold, the detected cardiac signal is identified as an R-wave at block 316.

A pacing escape interval may be restarted at block 318 in response to detecting the intrinsic R-wave at block 316. A pacing escape interval that was set previously by control module 206 at block 304 upon delivery of the stimulation pulse may be restarted without delivery of a pacing pulse by therapy delivery module 84.

Depending on the intrinsic cardiac rate and the duration of the polarization signal, additional intrinsic R-waves may be detected during the polarization signal. At block 320, the control module 80 or cardiac signal analyzer 90 may determine whether the polarization signal 102 has fallen below a threshold below which cardiac event sensing by sensing module 86 is deemed reliable. If not, post-stimulation R-wave detector 92 remains enabled and continues searching for another cardiac signal superimposed on the polarization signal 102 at block 310. If so, post-stimulation R-wave detector 92 may be disabled at block 322 until the next stimulation pulse is delivered. The electrical sensing module 86 may be enabled at block 324 to sense intrinsic events after the polarization signal has substantially decayed, enabling reliable amplitude-based cardiac event sensing using an auto-adjusted sensing threshold. As described above, electrical sensing module 86 may be enabled at block 324 when the polarization signal falls below the current R-wave sensing threshold automatically adjusted by electrical sensing module 86 based on a preceding R-wave peak amplitude.

Alternatively, the post-stimulation R-wave detector 92 is disabled at block 322 after a predetermined time interval after the most recent electrical stimulation pulse and the sensing module 86 is enabled at block 324 for sensing intrinsic R-waves until the next stimulation pulse is delivered at block 304. For example, searching for intrinsic events during the polarization signal 102 by post-stimulation R-wave detector using the methods shown by flow chart 300 or flow chart 200 may be enabled for up to 500 ms after a stimulation pulse, after which post-stimulation R-wave detector 92 is disabled and sensing module 86 is enabled for R-wave sensing.

Thus, a method and apparatus for sensing intrinsic cardiac electrical signals during a post-stimulation polarization signal following high-energy stimulation pulses have been presented in the foregoing description with reference to specific embodiments. In other examples, various methods described herein may include steps performed in a different order or combination than the illustrative examples shown and described herein. It is recognized, for example, that various aspects of a method for detecting intrinsic cardiac signals during post-stimulation polarization may include a different order or a different combination of steps than the order and combinations shown by the illustrative flow charts of FIGS. 5 and 6. Aspects of the two flow charts 200 and 300 may be implemented in any combination. It is appreciated that various modifications to the referenced embodiments may be made without departing from the scope of the disclosure and the following claims.

The invention claimed is:

1. A method comprising:
delivering a first electrical stimulation pulse to a patient that produces a post-stimulation polarization signal;
starting a pacing escape interval upon delivering the electrical stimulation pulse;
setting a blanking interval upon delivering the electrical stimulation pulse, the blanking interval extending beyond a time of an expected evoked response signal caused by the electrical stimulation pulse;
obtaining, after the blanking interval expires, an electrical signal sensed on an electrode vector, the electrical signal including a cardiac electrical signal superimposed on the post-stimulation polarization signal;
determining a feature of the sensed electrical signal;
comparing the feature of the sensed electrical signal to criteria for identifying an intrinsic cardiac event during the post-stimulation polarization signal;
identifying the intrinsic cardiac event when the feature meets the criteria;
restarting the pacing escape interval in response to identifying the intrinsic cardiac event; and
delivering a second electrical stimulation pulse in response to expiration of the pacing escape interval.

2. The method of claim 1, wherein:
determining the feature of the sensed electrical signal comprises determining a slope of the sensed electrical signal; and
wherein identifying the intrinsic cardiac event when the feature meets the criteria comprises identifying the intrinsic cardiac event when an acceleration of a decaying slope of the electrical signal is detected.

3. The method of claim 1, wherein:
determining the feature of the sensed electrical signal comprises determining a slope of the sensed electrical signal; and
wherein identifying the intrinsic cardiac event when the feature meets the criteria comprises identifying the intrinsic cardiac event when a change in a polarity of the decaying slope of the post-stimulation polarization signal is detected.

4. The method of claim 1, wherein:
determining the feature comprises determining if the sensed electrical signal is at least a biphasic signal having at least one positive-going peak relative to a decaying portion of the polarization signal and at least one negative-going peak relative to the decaying portion of the polarization signal;
identifying the intrinsic cardiac event comprises identifying the detected cardiac electrical signal as the intrinsic cardiac event when it is determined that the cardiac electrical signal is at least a biphasic signal.

5. The method of claim 1, wherein:
determining the feature comprises determining at least one of a signal width and a signal area of the detected cardiac electrical signal;
comparing the feature to the criteria comprises comparing at least one of the signal width and the signal area to a respective signal width threshold and a signal area threshold; and identifying the intrinsic cardiac event comprises identifying the intrinsic cardiac event when it is determined that at least one of the signal width and the signal area is less than the signal width threshold and the signal area threshold respectively.

6. The method of claim 1, further comprising:
establishing an intrinsic event waveform template;
wherein determining the feature of the sensed electrical signal comprises determining a waveform morphology of the sensed electrical signal;
wherein comparing the feature to the criteria comprises determining a correlation between the waveform morphology and the template and comparing the correlation to a threshold;
wherein identifying the intrinsic cardiac event comprises identifying the intrinsic cardiac event when it is determined that the correlation is greater than the threshold.

7. The method of claim 1, further comprising:
disabling a cardiac event sensing module during the post-stimulation polarization signal; and
enabling a cardiac signal analyzer during the post-stimulation polarization signal to detect the sensed electrical signal and identify the intrinsic cardiac event.

8. The method of claim 1, wherein delivering the electrical stimulation pulse comprises delivering the electrical stimulation pulse as one of a cardioversion/defibrillation shock pulse and an extracardiac pacing pulse having a pacing pulse energy greater than 1 milliJoule.

9. A medical device comprising:
a therapy delivery module configured to deliver a first electrical stimulation pulse to a patient that produces a post-stimulation polarization signal;
a control module configured to start a pacing escape interval upon delivery of the electrical stimulation pulse; and
a cardiac signal analyzer configured to:
set a blanking interval upon delivery of the electrical stimulation pulse, the blanking interval extending beyond a time of an expected evoked response signal caused by the electrical stimulation pulse;
obtain an electrical signal sensed across a pair of electrodes coupled to the medical device;
determine a feature of the sensed electrical signal;
compare the feature of the sensed electrical signal to criteria for identifying an intrinsic cardiac event during the post-stimulation polarization signal;
identify the intrinsic cardiac event if the feature meets the criteria;
wherein the control module is configured to restart the pacing escape interval in response to identifying the intrinsic cardiac event, and
wherein the therapy delivery module is configured to deliver a second electrical stimulation pulse in response to expiration of the pacing escape interval.

10. The device of claim 9, wherein the cardiac signal analyzer is configured to determine the feature by determining a slope of the sensed electrical signal and identify the intrinsic cardiac event when an acceleration of a decaying slope of the electrical signal is detected.

11. The device of claim 9, wherein the cardiac signal analyzer is configured to determine the feature by determining a slope of the sensed electrical signal and identify the intrinsic cardiac event when a change in a polarity of the decaying slope of the post-stimulation polarization signal is detected.

12. The device of claim 9, wherein the cardiac signal analyzer is further configured to:
determine the feature by determining if the sensed electrical signal is at least a biphasic signal having at least one positive-going peak relative to a decaying portion of the polarization signal and at least one negative-going peak relative to the decaying portion of the polarization signal;
identify intrinsic cardiac event when the sensed electrical signal is determined to be at least a biphasic signal.

13. The device of claim 9, wherein the cardiac signal analyzer is further configured to:
determine the feature by determining at least one of a signal width and a signal area of the detected cardiac electrical signal;
compare the feature to the criteria by comparing at least one of the signal width and the signal area to a respective signal width threshold and a signal area threshold; and
identify the intrinsic cardiac event by identifying the intrinsic cardiac event when it is determined that at least one of the signal width and the signal area is less than the signal width threshold and the signal area threshold respectively.

14. The device of claim 9, wherein the cardiac signal analyzer is further configured to:
establish an intrinsic event waveform template;
determine the feature of the sensed electrical signal by determining a waveform morphology of the sensed electrical signal;
compare the feature to the criteria by determining a correlation between the waveform morphology and the template and comparing the correlation to a threshold; and
identify the intrinsic cardiac event when it is determined that the correlation is greater than the threshold.

15. The device of claim 9, further comprising:
a cardiac event sensing module configured to set an auto-adjusting sensing threshold for sensing cardiac events within the electrical signal; and
a control module configured to:
disable the cardiac event sensing module during the post-stimulation polarization signal; and
enable the cardiac signal analyzer during the post-stimulation polarization signal to detect the cardiac electrical signal and identify the intrinsic cardiac event.

16. The device of claim 15, wherein the control module is further configured to re-enable cardiac event sensing module when the post-stimulation polarization signal falls below a threshold.

17. The device of claim 16, wherein the control module is further configured to disable the cardiac signal analyzer when the post-stimulation polarization signal falls below the threshold.

18. The device of claim 9, wherein the therapy delivery module is configured to deliver the electrical stimulation pulse as one of a cardioversion/defibrillation shock pulse and an extracardiac pacing pulse having a pulse energy of at least 1 milliJoule.

* * * * *